(12) United States Patent
Vidal Rodriguez et al.

(10) Patent No.: US 12,137,770 B2
(45) Date of Patent: Nov. 12, 2024

(54) WIDTH-AND LENGTH-ADJUSTABLE BOOT

(71) Applicant: VIDCAPP ITHEF SL, Serracines (ES)

(72) Inventors: Rafael Vidal Rodriguez, Serracines (ES); Aleksandar Lovic Jazbec, San Sebastian de los Reyes (ES); Miguel Cappiello Rodriguez, Geixo (ES)

(73) Assignee: VIDCAPP ITHEF SL, Serracines (ES)

(*) Notice: Subject to any disclaimer, the term of this patent is extended or adjusted under 35 U.S.C. 154(b) by 418 days.

(21) Appl. No.: 17/413,836

(22) PCT Filed: Dec. 15, 2018

(86) PCT No.: PCT/ES2018/070806
§ 371 (c)(1),
(2) Date: Jun. 14, 2021

(87) PCT Pub. No.: WO2020/120811
PCT Pub. Date: Jun. 18, 2020

(65) Prior Publication Data
US 2022/0079283 A1    Mar. 17, 2022

(51) Int. Cl.
*A43B 3/26* (2006.01)
(52) U.S. Cl.
CPC .................................. *A43B 3/26* (2013.01)
(58) Field of Classification Search
CPC ........... A43B 3/26; A43B 5/1608; A43B 5/04; A43B 13/16; A43B 23/0295; A43B 5/0435; A43B 5/045; A43B 3/24; A43B 3/16; A43B 5/18; A63C 17/0086; A63C 2203/48; A63C 1/26; A63C 13/006; A43D 1/02; A43C 15/068; A43C 15/061; A43C 15/06; A43C 15/063; A43C 15/065; A43C 15/066; A43C 15/02

USPC .............................................................. 36/97
See application file for complete search history.

(56) References Cited

U.S. PATENT DOCUMENTS

| 452,284 A | * | 5/1891 | Reilly | A43C 15/06 |
| | | | | 15/267 |
| 1,316,251 A | * | 9/1919 | MacWilliam | A63C 17/02 |
| | | | | 280/11.32 |
| 4,083,128 A | | 4/1978 | Rossman | |
| (Continued) | | | | |

FOREIGN PATENT DOCUMENTS

EP                443293 A   *   8/1991   ............... A43B 3/26

OTHER PUBLICATIONS

Translation of EP-443293-A (Year: 1991).*

*Primary Examiner* — Sharon M Prange
*Assistant Examiner* — Grady Alexander Nunnery
(74) *Attorney, Agent, or Firm* — Defillo & Associates, Inc; Evelyn A. Defillo

(57) ABSTRACT

A length- and width-adjustable boot including: a forward base component (BA), a rearward base component (BP), a right side (LR), a left side (LL), and a locking system for said components. The four components (BA, BP, LR, LL) are linked together by rails. The slope of the rails of one of the bases (BP or BA), with regard to the axis of symmetry of the base of the boot, is determined by the length/width ratio of the foot. The movement of any of the four components causes a movement proportional to the width and length of the foot in the other three. The locking system locks the four components of the boot to be worn.

3 Claims, 8 Drawing Sheets

(56) References Cited

U.S. PATENT DOCUMENTS

| | | | | |
|---|---|---|---|---|
| 6,092,306 A | * | 7/2000 | Newton-Dunn | ......... A43B 5/18 36/7.1 R |
| 2004/0107605 A1 | | 6/2004 | Caeran | |
| 2016/0000174 A1 | | 1/2016 | Grim | |

* cited by examiner

WIDTH-AND LENGTH-ADJUSTABLE BOOT

CROSS REFERENCE TO RELATED APPLICATION

This application is a national stage entry of PCT/ES2018/070806 filed Dec. 15, 2018, under the International Convention.

FIELD OF THE INVENTION

As the title of the invention establishes, the object of this invention is a length- and width-adjustable boot, that is, the boot allows a width and length adjustment for different foot dimensions of different users.

Moreover, this invention takes into account the fact that the anatomy of the foot maintains the same length-to-width ratio regardless the size of the foot. E.g. a person with a 36 European foot, will have the same length/width ratio as a person with a 46 foot.

Therefore, we get a boot for different uses such as medical use (post-traumatic immobilization, post-surgical immobilization, rehabilitation), sports use (skating, skiing, water skiing and other sports that use boots), or work use (safety boots), allowing its use in a wide range of sizes or foot size.

Furthermore, the present invention achieves such change in proportions (width and length), simply by tightening a single screw in the heel of the boot.

BACKGROUND OF THE INVENTION

Currently the boots for use in the sports field, and some areas of medical use (walker boots), are marketed in different sizes; with respect to the manufacturing level, this implies higher costs in production, molds and storage; and even so many times the different sizes are not fit properly to foot size.

In the specific case of walker boots, these stand out for allowing an increased activity of the patient and accelerate the recovery period of injuries, and in this way, avoid a greater loss of muscle tone very frequent after long periods of immobilization with other systems like plasters.

The walker boot is a very functional immobilization, both for the patient as for the professionals who supervise the treatment.

The walker boots on the market offer a very limited number of sizes, so they do not allow adequate adaptation and compression to the foot necessary during the treatment of injuries. To achieve the proper adaptation and immobilization some existing models incorporate a camera of air (foams, sponges) to fill in the gaps between the boot cover and the ankle. Also, account must be taken of the fact that the volume of the injured foot changes during the healing process, so sometimes a new boot of a different size is required at a certain point in the treatment.

Therefore, it is the object of the present invention to develop a boot that allows continuous adjustment, and thus a better adaptation to the user's foot, to while eliminating production and warehousing problems (storage of a multitude of sizes), developing a boot like the one that is described below, and is collected in its essentiality in the first claim.

DESCRIPTION OF THE INVENTION

The object of the present invention is an adjustable boot that covers a wide range of foot sizes, which in a possible embodiment can cover from a foot size corresponding to 36 EU to 46 EU.

The boot is made up of four pieces assembled together using rail plus a fixing system, so that the displacement of one of the four pieces produces the corresponding displacement of the rest of the pieces proportionally and anatomically, that is, it is a displacement that corresponds to the width and length of the foot.

Said four pieces are, a forward base component (BA), a rearward base component (BP), a left side (LL), and a right side (LR).

In a preferred embodiment, the forward and rearward bases form an inverted isosceles trapezium (due to the shape of the foot, wider in the front than in the heel). Having determined the inclination of the sides of the trapezium with respect to its axis of symmetry, by the relationship between the width of the forefoot and the heel.

Preferably, the fixation system is a screw, which is located on the axis of symmetry of the aforementioned trapezium. This screw runs through the forward base, is screwed into the rearward base, and is fixed to the assembly by means of a ring safety or circlip. So that a movement of the screw in the clockwise movement produces an approach of the forward and rearward bases, and a counterclockwise movement causes a separation or distance. Thus, provoking a change in the length of the total base of the boot. (Being the total base of the boot, the forward base plus the rearward base plus the space between both of them).

The rearward base also has guide rail (BPr1, BPr2) for those that run or slide the left (LL) and right (LR) side pieces. The angle $\alpha$ of inclination of these rail with respect to the axis of symmetry of the boot is determined by the length/width ratio of the foot In turn, each side has two rails at the bottom, the left side (LLr1, LLr3) and the right side (LRr2, LRr4). The LLr1 and LRr2 rail fit on the rearward base, and LLr3 and LRr4 on the forward base.

The rail on the sides that fit into the rearward base (LLr1, LRr2), allow a movement between the rearward base, and both sides right and left. The direction of movement of these parts is determined by the angle $\alpha$.

The rail on the sides that attach to the forward base (LLr3, LRr4), allow a movement between pieces (forward base and sides), in the direction perpendicular to the axis of symmetry of the total base of the boot, that is, towards the outside of each side.

This system of four rail, two on the forward base, and two on the rearward base, is the one that allows that when a movement occurs in one of the four pieces, this movement is transferred to the rest of the set. And because of that, when a clockwise movement is exerted on the screw described above, there is an approach between the forward and rearward bases, and an approach of the sides; the boot gets shorter, and narrower. And on the other hand, when a counterclockwise movement is exerted on the screw, the forward and rearward bases move away, and the laterals separate; the boot becomes wider and longer.

Unless otherwise indicated, all technical and scientific elements used herein have the meaning that is usually understood by an average expert on the matter in the state of art to which this invention pertains. Procedures and materials may be used in the practice of the present invention which are similar or equivalent to the ones described in the specifications.

Throughout the description and claims the word "comprises" and its variants are not intended to exclude other technical characteristics, additives, components or steps. For the experts on the matter, other objects, advantages and characteristics of the invention will emerge in part from the description and in part from the practice of the invention.

EXPLANATION OF THE FIGURES

To complement the description that is being made and in order to help a better understanding of the characteristics of the invention, it is enclosed as an integral part of the said description, a set of drawings in where, for illustrative and non-limiting purposes, the following has been represented.

PREFERRED EMBODIMENT OF THE INVENTION

Figure 1:
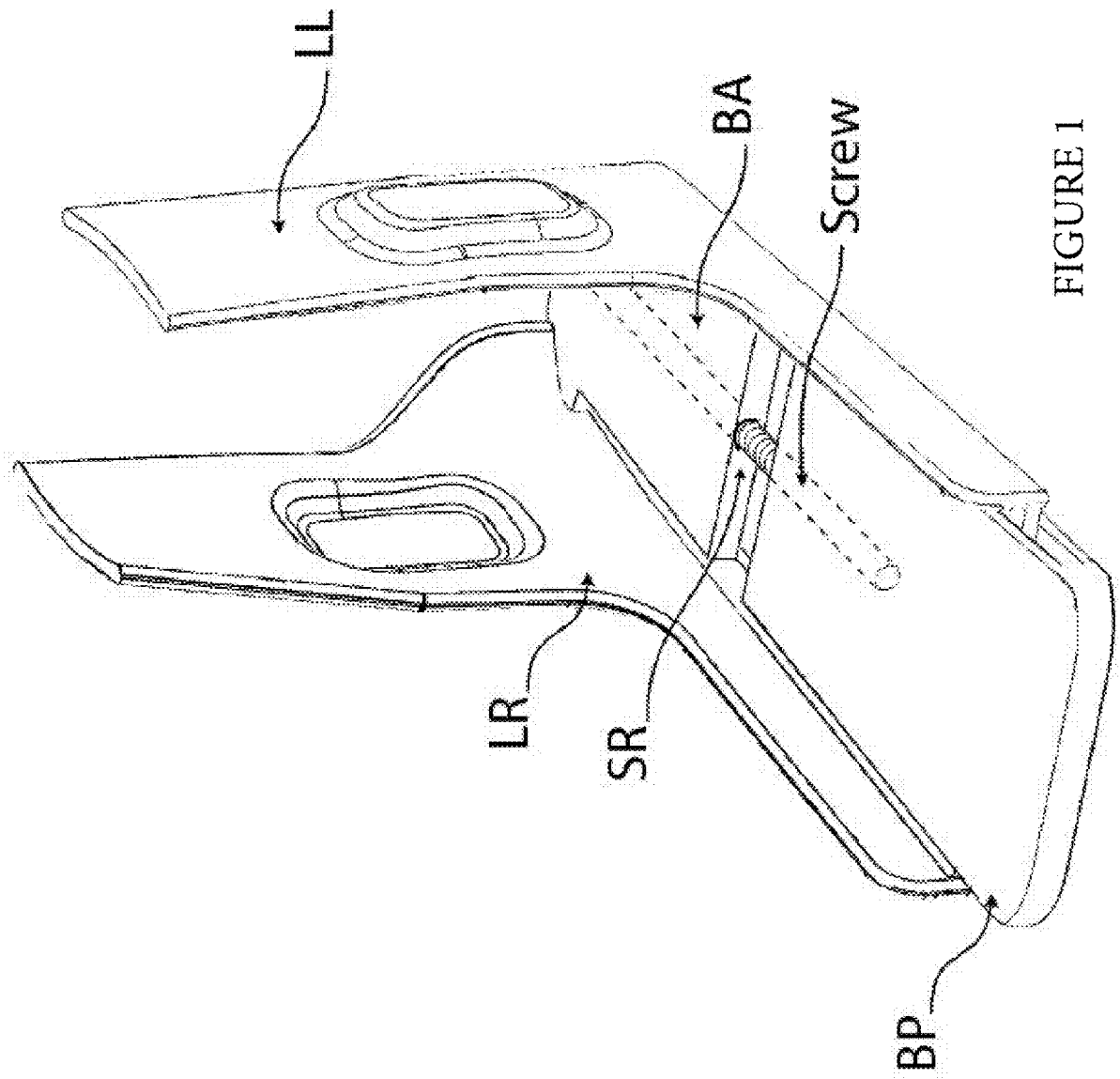
FIG. 1—You can see a 3D design of the set of parts. Forward base (BA), rearward base (BP), left side (LL), right side (LR), fixing screw (Screw), and safety ring (SR).
Figure 2:
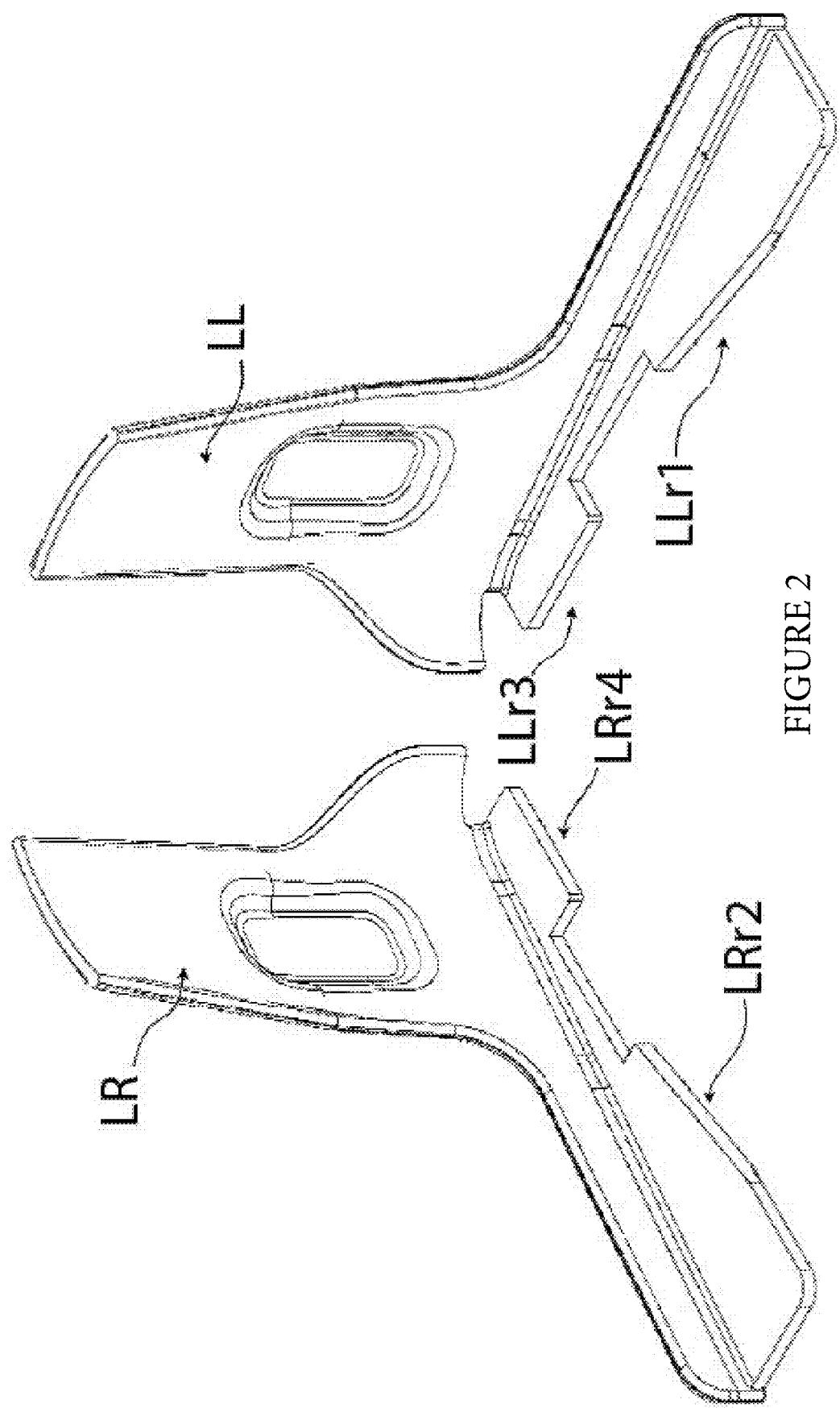
FIG. 2—you can see a 3D design of the right side (LR) and left side (LL) with their respective rail LRr2, LRr49 and LLr1, LLr2.
Figure 3:
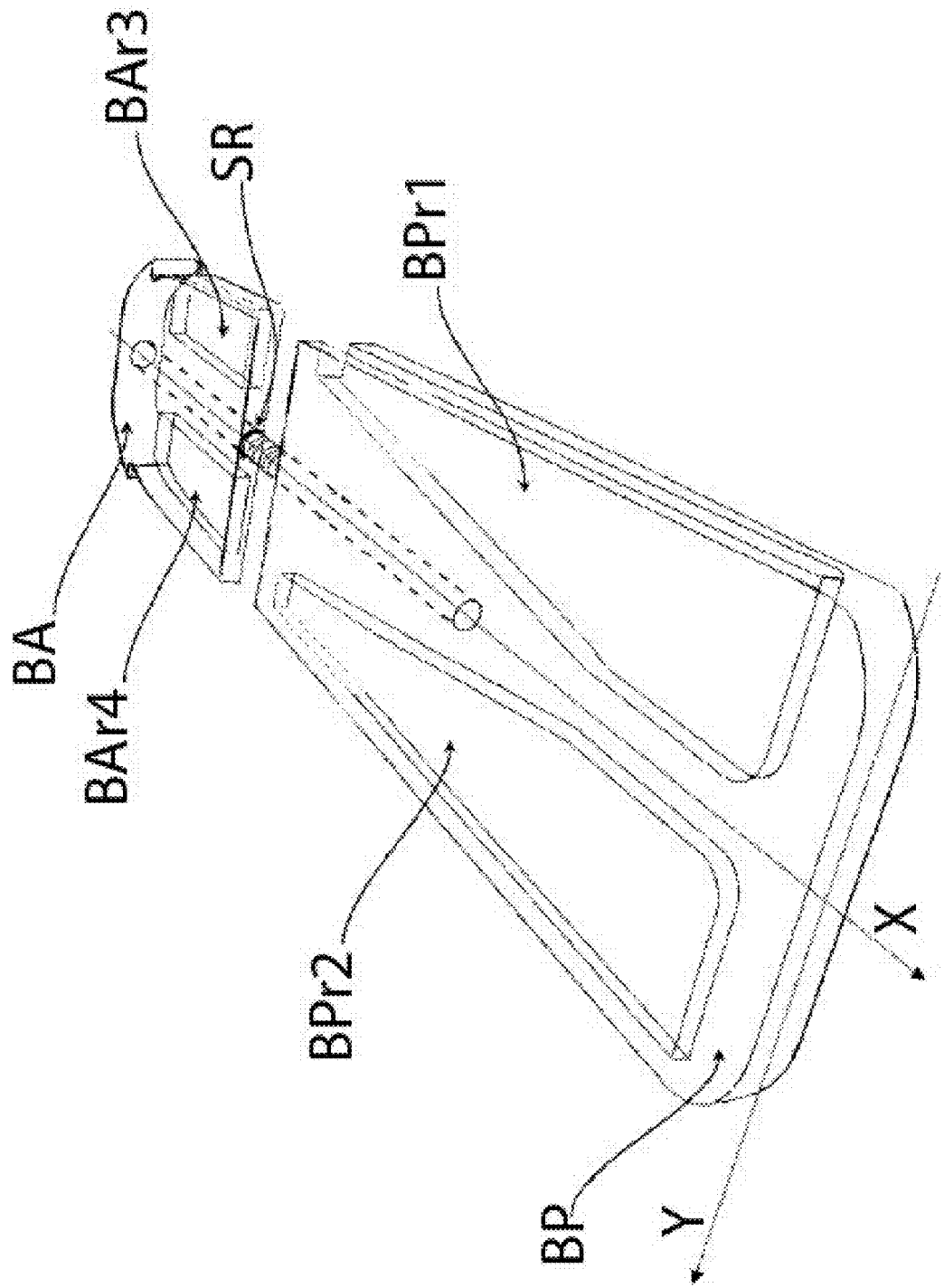
FIG. 3—you can see a 3D design of the forward base (BA) and rearward base (LR), with their respective rail. The pieces have been made transparent to be able to appreciate the inner rail BPr1, BPr2 and BAr3, BAr4.

In FIG. 1 we can see that the boot object of the invention comprises:
1. a rearward base piece (BP)
2. a forward base piece (BA)
3. a right side piece (LR)
4. a left side piece (LL)
5. an adjusting and fixing screw (Screw)

The four pieces, forward base, rearward base, right side and left side are connected to each other by rail. The rearward base has two inner rail (BPr1, BPr2). The inclination of these rail with respect to the axis of symmetry of the boot is determined by a. The forward base piece has two inner rail (BAr3, BAr4) perpendicular to its axis of symmetry.

The side pieces have two rail each. The right side piece (LR) has a rail with the first projection LRr2 and a second projection LRr4, and the left side piece (LL) has rail with the first projection LLr1 and a second projection LLr3. So that the first projection LLr1 of the left side piece and the first projection LRr2 of the right side piece couple into the rail of the rearward base (BPr1, BPr2), and the second projection LLr3 of the left side piece and second LRr4 of the right side piece on the rail of the forward base (BAr3, BAr4).

Any displacement of one of the four pieces causes a displacement in the other three.

To adjust and fix the assembly of parts in a simple way, a screw (Screw) is placed at the back of the forward based piece (BA). This screw runs along the axis of symmetry of the rearward base, thread in the rearward base piece (BP), and is fixed to the assembly by means of a safety ring or circlip.

When the screw threads clockwise (screw tightening), the forward and rearward bases are closer to each other (the boot becomes shorter), and the sides also get closer to each other (the boot becomes narrower). When the screw rotates counterclockwise, the opposite effect occurs, the bases (BA, BP), and the laterals (LL, LR) move away, making the boot wider and longer.

The angle $\alpha$ determines the ratio between the length and width of the boot each time it is acted on the fixing screw. And the angle $\beta$ determines the trapezoidal shape of the base of the boot due to the difference in width between the heel of the foot, and the instep.

Figure 4:
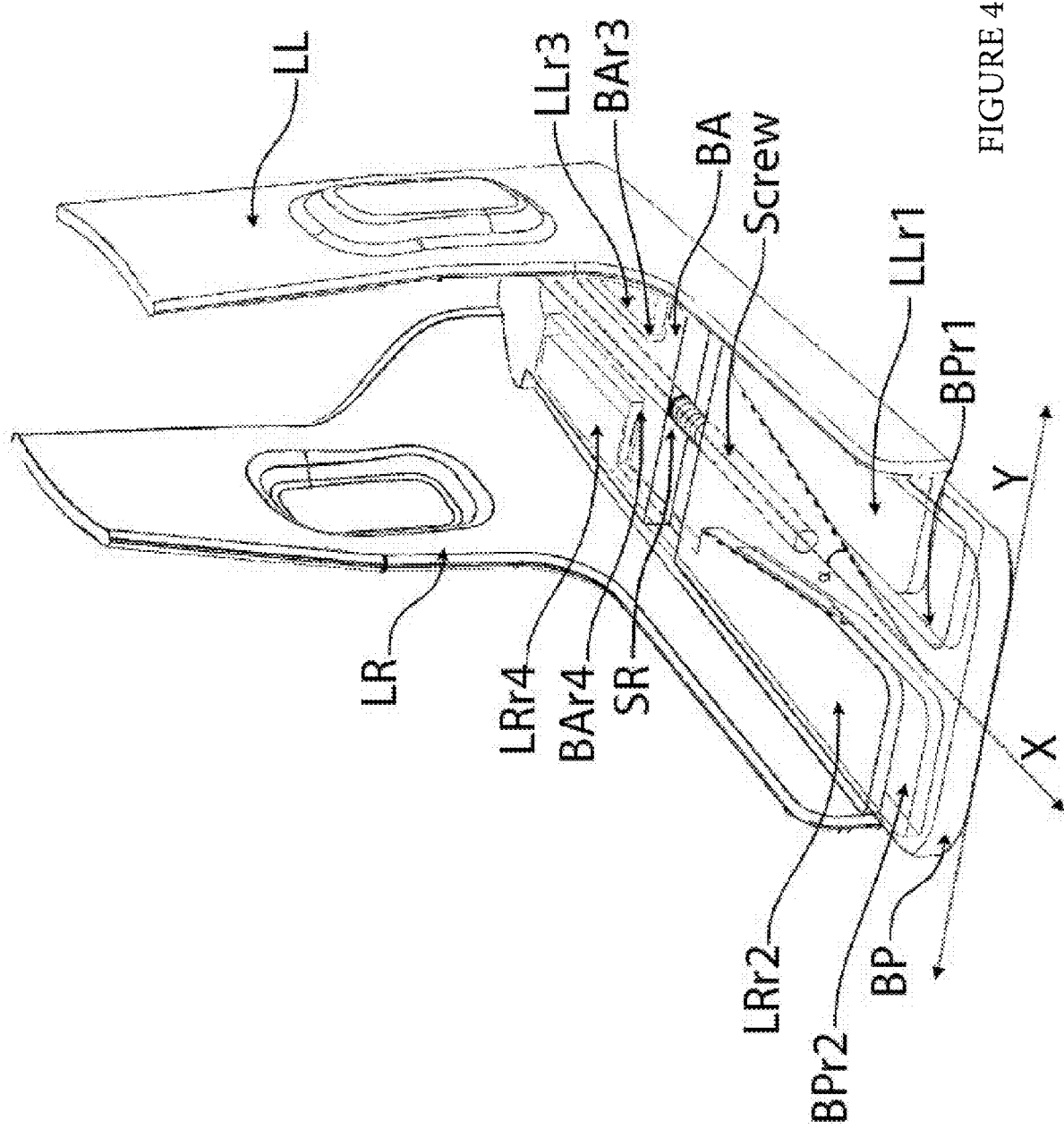
FIG. 4—you can see a 3D design of the whole set of parts, BA, BP, LL, LR, fixing screw (Screw), and safety ring (SR). The forward base (BA) and rearward base (BP) have been made transparent so that all the rail can be appreciated. The angle $\alpha$ can also be seen drawn, which indicates the inclination of the rail of the rearward base (BP), with respect to the axis of symmetry of the boot (X axis).
Figure 5:
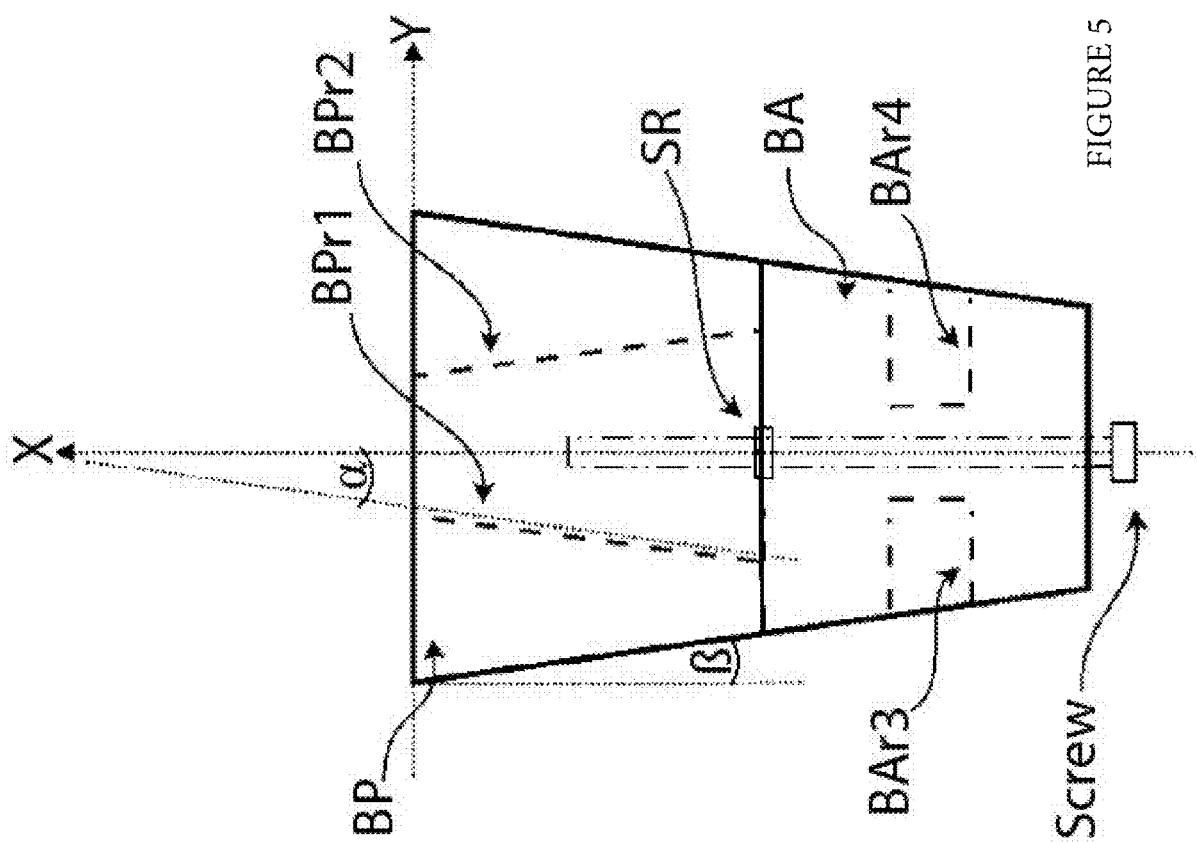
FIG. 5—you can see a simple conceptual scheme, made up of the forward base (BA) and the rearward base (BP), and a screw (Screw), which runs through the axis of symmetry X. The inverted trapezoid shape of the total forefoot base comes determined by the ratio of the width of the forefoot to the heel (angle $\beta$). Two rails run inside the rearward base (BP) (BPr1, BPr2), inclined. The angle $\alpha$ of inclination of the rail determines the foot length/width ratio.
Figure 6:
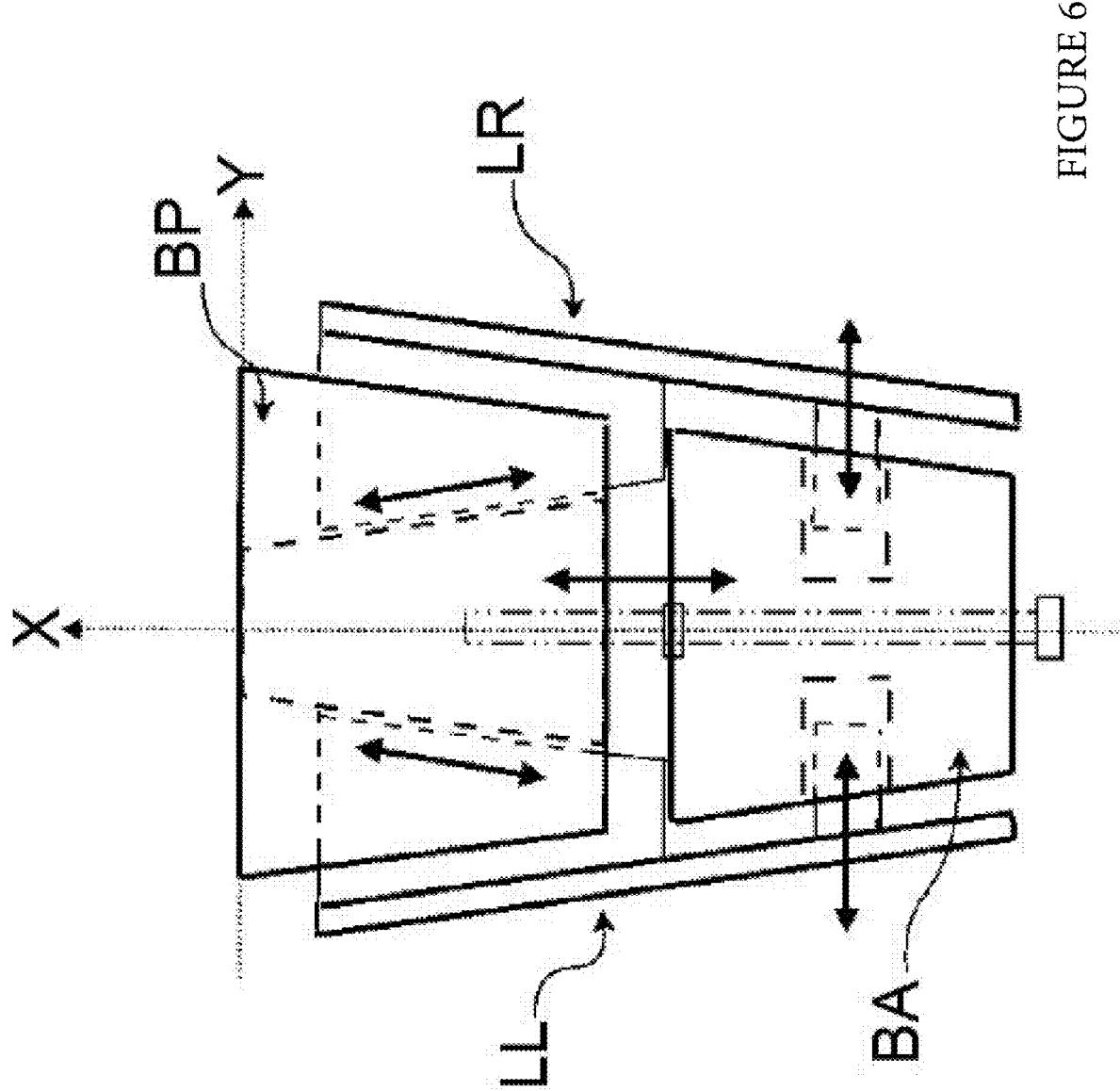
FIG. 6—you can see a simple conceptual diagram in which the pieces BA, BP, LL, LR are represented joined by the rail. Arrows indicate the directions of movement of all the pieces along their respective rail.
Figure 7:
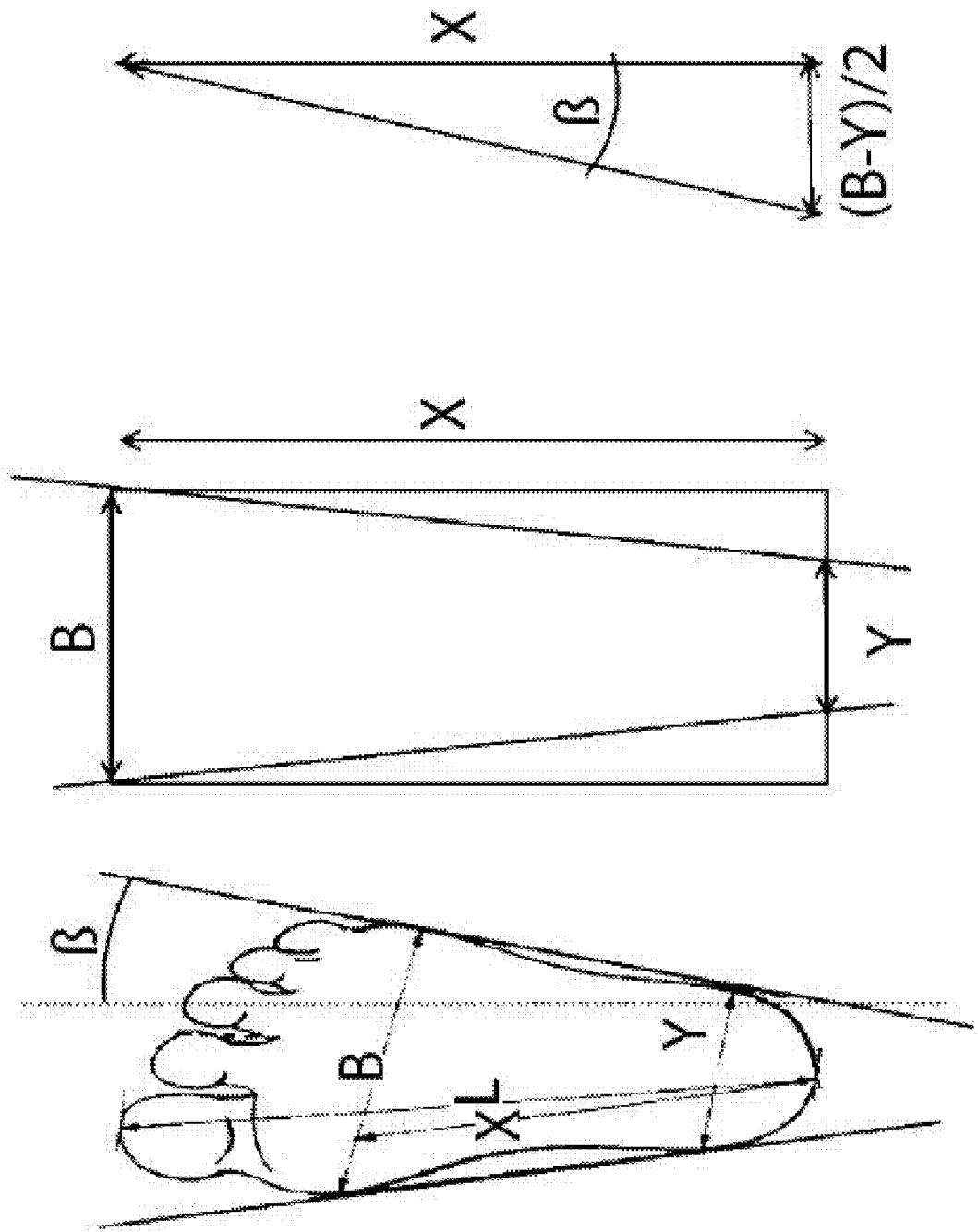
FIG. 7—you can see the calculation of the angle Alpha, $\alpha$=arc tg B/L.
Figure 8:
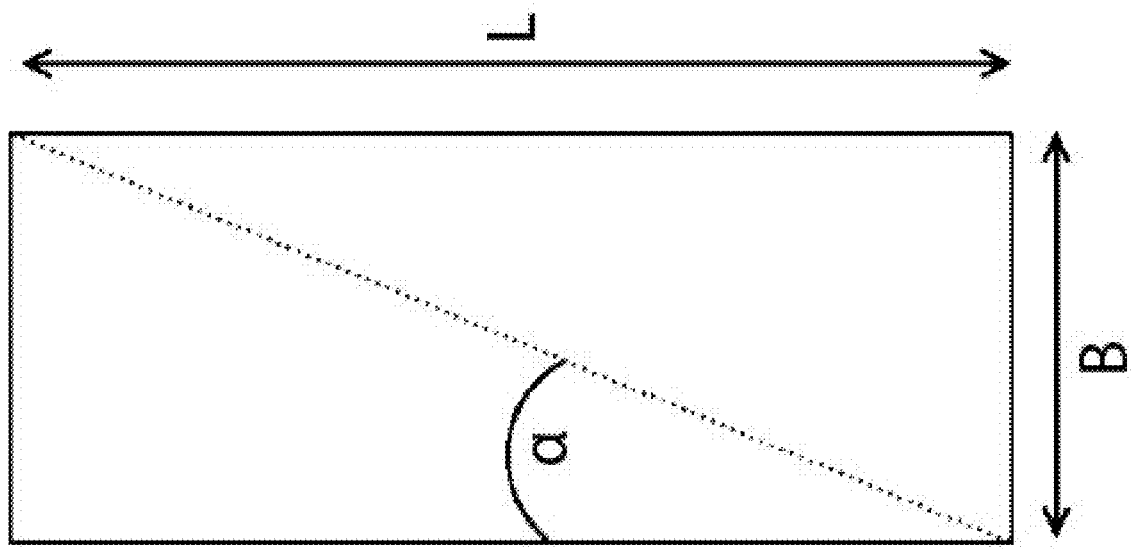
FIG. 8—you can see the calculation of the angle Beta, $\beta$=arctg (B−Y)/2/X).
Figure 8:
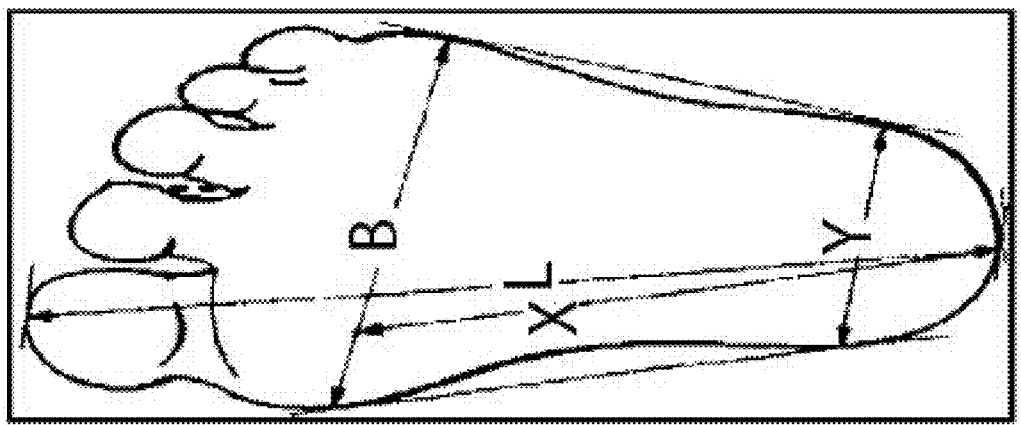

To calculate the angles $\alpha$ and $\beta$, we take into account the anatomical tables of Chockalingham (REF: Chockalingam N & Ashford RL (2002) Foot length ratios for selected dimensions in a non clinical male simple). According to these tables, approximate ratios for the dimensions of the foot are fulfilled. Dimensions X, Y, B, L, and calculation of the angles $\alpha$ and $\beta$ are described in FIGS. 4 and 5.

| L/B = 3.3 | L/Y = 5.5 | L/X = 1.3 |
| --- | --- | --- |

Therefore, for L=1 we have Y=0.18, B=0.3 and X=0.77.

$\beta$=arctg(B−Y)/2/X;$\beta$=4.5°

$\alpha$=arc tg B/L;tg a=B/L;$\alpha$=16.85°

The length of the forward and rearward bases, and the length of the set screw determine the range of foot sizes that the boot is suitable for.

Thus, for a minimum foot size 36 EU (22 cm), the forward and rearward bases must add up to 22 cm in length. And for a maximum foot size of 46 EU (28.5 cm), the adjusting screw should measure at least the length of the base above plus the difference in length between sizes.

Sufficiently described the nature of the present invention, as well as the way of putting it into practice, it is stated that, within its essentiality, may be put into practice in other embodiments that differ in detail of the one indicated by way of example, and to which the protection that is sought will also reach, provided that there is no alteration, change or modification of its fundamental principle.

The invention claimed is:

1. A length- and width-adjustable boot comprising:
a rearward base piece (BP) including a left rearward inner rail (BPr1) and a right forward inner rail (BPr2), the rearward base piece (BP) having a shape of an inverted isosceles trapezium, the left rearward inner rail and the right forward inner rail have an inclination with respect to an axis of symmetry of the boot with an angle $\alpha$ determined by a length/width ratio of a foot comprised between 0° and 90°;
a forward base piece (BA) having a left forward inner rail (BAr3) and right forward inner rail (BAr4), the forward base piece (BA) having a shape of an inverted isosceles trapezium, the left forward inner rail and the right forward inner rail are perpendicular to the axis of symmetry of the boot;

a right-side piece (LR) with a bottom end having a first rail (LRr2) on a first side and a second rail (LRr4) on a second side, wherein the first rail (LRr2) slides into the right forward inner rail (BPr2) of the rearward base piece and wherein the second rail (LRr4) slides into the right forward inner rail (BAr4) of the forward base piece;

a left-side piece (LL) having at a bottom end a first rail (LLr1) on a first side and a second rail (LLr3) on a second side, wherein the first rail (LLr1) of the left side piece slides into the left rearward inner rail (BPr1) of the rearward base piece (BP) and wherein the second rail (LLr3) slides into the left inner rail (BAr3) of the rearward base piece (BA);

a one-piece fixing device runs through the forward base piece and is screwed into the rearward base piece, the one-piece fixing device moves the rearward base piece (BP), the forward base piece (BA), the left-side piece (LL) and the right-side piece (LR) simultaneously, so that a movement of any one of the rearward base piece (BP), the forward base piece (BA), the left-side piece (LL), or the right-side piece (LR) produces a simultaneous movement to adjust a width and a length of the boot in the other three of the rearward base piece (BP), the forward base piece (BA), the left-side piece (LL), and the right-side piece (LR).

2. The length- and width-adjustable boot according to claim 1, wherein the one-piece fixing device is a threaded screw placed at a back side of the forward base piece (BA) and runs along the axis of symmetry of the boot, the threaded screw runs through the forward base piece (BA) and is screwed into the rearward base piece, the threaded screw is secured with a safety ring.

3. The length- and width-adjustable boot according to claim 1, wherein the angle $\alpha$ is determined by the following equation:

$$\alpha = \operatorname{arctg} B/L$$

wherein:
L is the length of the foot;
B is the width of the foot.

* * * * *